United States Patent [19]
Abrignani

[11] Patent Number: 6,074,635
[45] Date of Patent: Jun. 13, 2000

[54] T CELL ACTIVATION

[75] Inventor: Sergio Abrignani, Vagliagli, Italy

[73] Assignee: Chiron Corporation, Emeryville, Calif.

[21] Appl. No.: 08/776,259

[22] PCT Filed: Aug. 17, 1995

[86] PCT No.: PCT/IB95/00691

§ 371 Date: Jan. 21, 1997

§ 102(e) Date: Jan. 21, 1997

[87] PCT Pub. No.: WO96/05288

PCT Pub. Date: Feb. 22, 1996

[30] Foreign Application Priority Data

Aug. 17, 1994 [GB] United Kingdom ............... 9416657

[51] Int. Cl.$^7$ ........................... A61K 45/00; A61K 39/00
[52] U.S. Cl. ................. 424/85.1; 424/85.2; 424/185.1
[58] Field of Search ............................ 424/185.1, 851, 424/852

[56] References Cited

U.S. PATENT DOCUMENTS

| | | | |
|---|---|---|---|
| 4,879,111 | 11/1989 | Chong | 424/85.2 |
| 5,091,511 | 2/1992 | Sone et al. | 530/351 |
| 5,425,940 | 6/1995 | Zimmerman et al. | 424/85.1 |

OTHER PUBLICATIONS

J. Bryne et al., "Differential Activation Requirements For Virgin and Memory T Cell", *J. Immunol.* (1988) 141(10):3249–3257.

S. Carding et al., "Activation of Cytokine Genes in T Cells during Primary and Secondary Murine Influenza Pneumonia", *J. Exp. Med.* (1993) 177:475–482.

A. Chinn et al., "T Cell Proliferative Response to Interleukin 2: Different Frequency of Responders Among CD45RO and CD45RA Subsets", *Cellular Immunology* (1990) 131(1):132–139.

N. Damle et al., "Distinct Regulatory Effects of IL–4 and TNF–α During CD3–Dependent and CD3–Independent Initiation of Human T–Cell Activation", *Lymphokine Research* (1989) 8(2):85–97.

J. Depper et al., "Interleukin 2 (IL–2) Augments Transcription of the IL–2 Receptor Gene", *Proc. Natl. Acad. Sci. USA* (1985) 82:4230–4234.

J. Farrar et al., "Thymoma Production of T Cell Growth Factor (Interleukin 2)", *J. Immunol.* (1980) 125(6):2555–2558.

R. Garman et al., "B–Cell–Stimulatory Factor 2 (β2 Interferon) Functions as a Second Signal for Interleukin 2 Production by Mature Marine T Cells", *Proc. Natl. Acad. Sci. USA* (1987) 8:7629–7633.

D. Gray, "Immunological Memory: A Function of Antigen Persistance", *Trends in Microbiology* (1993) 1(2):39–42.

Z. Grossman et al., "Adaptive Cellular Interactions in the Immune System: The Tunable Activation Threshold and the Significance of Subthreshold Responses", *Proc. Natl. Acad. Sci. USA* (1992) 89:10365–10369.

K. Horgan et al., "Hyporesponsiveness of "Naïve" (CD45RA+) Human T Cells to Multiple Receptor–Mediated Stimuli but Augmentation of Responses by Co–Stimuli", *Eur. J. Immunol.* (1990) 20:1111–1118.

I. Lefkovits et al., "Limiting Dilution Analysis of the Cells of Immune System I. The Clonal Basis of the Immune Response", *Immunology Today* (1984) 5(9):265–268.

M. Minutello et al., "Compartmentalization of T Lymphocytes to the Site of Disease: Intrahepatic CD4+ T Cells Specific for the Protein NS4 of Hepatitis C Virus in Patients with Chronic Hepatitis C", *J. Exp. Med.* (1993) 178:17–25.

M. Ostensen et al., "Tumor Necrosis Factor–α Enhances Cytolytic Activity of Human Natural Killer Cells", *J. Immunol.* (1987) 138(12):4185–4191.

L. Owen–Schaub et al., "Regulation of Lymphocyte Tumor Necrosis Factor Receptors by IL–2" *J. Immunol.* (1989) 143(7):2236–2241.

W. Paul, "*Fundamental Immunology*, 3$^{rd}$ Edition Raven Press, New York", (1993) pp. 766–768, 807–815, 966–970.

S. Romagnani et al., "Cytokines: Basic Principles and Practical Applications", *Challenges Mod. Med.* (1994) 8:49–52.

S. Rosenberg et al., "Observations on the Systemic Administration of Autologous Lymphokine–Activated Killer Cells and Recombinant Interleukin–2 to Patients with Metastatic Cancer", *The New England Journal of Medicine* (1985) 313(23):1485–1486.

P. Scheurich et al., "Immunoregulatory Activity of Recombinant Human Tumor Necrosis Factor (TNF)–α: Induction of TNF Receptors on Human T Cells and TNF–α–Mediated Enhancement of T Cell Responses", *J. Immunol.* (1987) 138(6):1786–1790.

I. Schmid et al., "A Gentle Fixation and Permeabilization Method for Combined Cell Surface and Intracellular Staining With Improved Precision in DNA Quantification", *Cytometry* (1991) 12:279–285.

J. Sleasman et al., "The Role of Functionally Distinct Helper T Lymphocyte Subpopulations in the Induction of Human B Cell Differentiation", *Eur. J. Immunol.* (1990) 20:1357–1366.

K. Smith, "Lowest Dose Interleukin–2 Immunotherapy", *Blood* (1993) 81(6):1414–1423.

H. Teh et al., "Activation of Nonspecific Killer Cells by Interleukin 2–Containing Supernatants", *J. Immunol.* (1983) 131(4):1827–1833.

R. Testi et al., "LEU 23 Induction as an Early Marker of Functional CD3/T Cell Antigen Receptor Triggering Requirement for Receptor Cross–Linking, Prolonged Elevation of Intracellular [Ca++] and Stimulation of Protein Kinase C", *J. Immunol.* (1989) 142(6):1854–1860.

(List continued on next page.)

*Primary Examiner*—David Saunders
*Assistant Examiner*—Mary Beth Tung
*Attorney, Agent, or Firm*—Doreen Y. Trujillo; Alisa A. Harbin; Robert P. Blackburn

[57] ABSTRACT

Methods for activating T cells in the absence of antigen, and compositions for effecting the same, are described.

6 Claims, 11 Drawing Sheets

OTHER PUBLICATIONS

M. Tsudo et at., "Characterization of the Interleukin 2 Receptor β Chain Using Three Distinct Monoclonal Antibodies", *Proc. Natl. Acad. Sci. USA* (1989) 86:1982–1986.

D. Unutmaz et al., "Antigen–Independent Activation of Naive and Memory Resting T Cells by a Cytokine Combination", *J. Exp. Med.* (1994) 180:1159–1164.

A. Vink et al., "Accessory Factors Involved in Murine T Cell Activation. Distinct Roles of Interleukin 6, Interleukin 1 and Tumor Necrosis Factor", *Eur. J. Immunol.* (1990) 20:1–6.

C. Weaver et at., "The Costimulatory Function of Antigen–Presenting Cells", *Immunology Today* (1990) 11(2):49–55.

S. Abrignani et al., "Priming of CD4+ T Cells Specific for Conserved Regions of Human Immunodeficiency Virus Glycoprotein GP120 in Humans Immunized with a Recombinant Envelope Protein", *Proc. Natl. Acad. Sci. USA.*, (1990) 87:6136–6140.

A. Akbar et al., "Loss of CD45R and Gain of UCHL1 Reactivity is a Feature of Primed T Cells", *J. Immunol.* (1988) 140(7):2171–2178.

A. Akbar et al., "Cellular Events During Memory T–Cell Activation In Vitro: The UCHL1(180,000 MW) Determinant is Newly Synthesized after Mitosis", *Immunology* (1989) 66:213–218.

S. Akira et al., "Biology of Multifunctional Cytokines: IL 6 and Related Molecules (IL 1 and TNF)", *FASEB* (1990) 4:2860–2867.

W. Benjamin et al., "Production of Immune Interferon by an Interleukin 2–Independent Murine T Cell Line", *Proc. Natl. Acad. Sci.USA* (1982) 79:5379–5383.

P. Beverley et al., "Is T–Cell Memory Maintained by Cross-reactive Stimulation?", *Immunology Today* (1990) 11(6):203–205.

L. Bradley et al., "T–Cell Memory: New Perspectives", *Immunology Today* (1993) 14(5):197–199.

Paul, W.F. (ed.), Fundamental Immunology, 3rd edition, pp. 766–768, 807–815, 966–970, 1993.

Paul, WE, Fundamental Immunology, Lippincott–Raven, Philadelphia pp. 576–579, 1999.

T CELL ACTIVATION

This application was filed under 35 U.S.C. 371, and claims priority to PCT/IB95/00691, filed Aug. 17, 1995, which claims priority to Great Britain patent application 9416657.6, filed Aug. 17, 1994.

FIELD OF THE INVENTION

The present invention relates to an antigen independent method for the activation of T cells. The invention also relates to a method for increasing lymphokine production in a T cell culture and a method for increasing the immune response at specific sites in vivo which has therapeutic applications in the treatment of disease.

BACKGROUND OF THE INVENTION

T cells are involved in the immune response and are primarily involved in cellular immunity, such as guarding against virally infected cells, fungi, parasites and foreign tissue.

Briefly, T cells are activated by binding to antigen-displaying macrophages. However, the T cell receptor must specifically complex with the antigen and a Major Histocompatibility Complex (MHC) protein displayed on the surface of the macrophage.

The binding induces the macrophage to release interleukin-1, a polypeptide growth factor, which stimulates the bound T cell to proliferate and differentiate. This proliferation and differentiation is enhanced by the T cells autostimulatory secretion interleukin-2. The T cell can differentiate into a number of different phenotypes, such as cytotoxic T cells which are specifically targeted to antigen displaying host cells and are capable of lysing the cell, helper T cells which are involved in activating cytotoxic T cells and in co-operating with B cells to produce antibodies and memory T cells which upon re-encountering their cognate antigen proliferate at a faster rate than non-memory T cells.

It will be apparent to one skilled in the art that the activation of T cells is an important step in the immunological response. By manipulating the activation of T cells it will be possible to obtain useful immunological products and develop more efficient treatment techniques.

Previously, to achieve T cell activation, a macrophage displaying an antigen and an MHC protein was required. A number of problems and drawbacks are associated with this, a major drawback being that only T cells specific for the antigen are activated. Other T cells not specific for the antigen remain unactivated. Other problems may arise if the desired antigen is difficult to obtain or hazardous to work with. Additionally, if an antigen is used in cell culture to achieve activation and it is not easy to remove, contamination problems may occur.

The same problems will occur in vivo and it is obviously undesirable to infect an individual with an antigenic substance.

By achieving antigen independent T cell activation it will be possible to activate a population of T cells without the need to isolate and display an antigen on the surface of a macrophage.

It is known that interleukin-2 is potent T-lymphocyte growth enhancer and the use of interleukin-2 as an adjuvant has been described. In this role interleukin-2 was thought to function as an expander of the population of already activated T-lymphocytes. However, it was not known that interleukin-2 (in combination with other cytokines) could act specifically to activate T-lymphocytes in an antigen independent manner.

SUMMARY OF THE INVENTION

According to the present invention there is provided a method for antigen independent activation of T cells comprising contacting T cells with a combination of cytokines.

Preferably, the T cells are contacted with at least two of the following:
 i) interleukin-2;
 ii) interleukin-6; and
 iii) tumour necrosis factor α
or functionally equivalent fragments thereof.

The T cells may be naive T cells and/or memory resting T cells, most suitably naive $CD45RA^+$ cells and/or memory resting $CD45RO^+$ cells.

Suitably, the concentration of interleukin-2 is from 100 to 400 U/ml, the concentration of interleukin-6 is from 400 to 600 U/ml and the concentration of tumour necrosis factor α is from 15 to 35 ng/ml. More preferably, the concentration of interleukin-2 is from 200 to 300 U/ml, the concentration of interleukin-6 is about 500 U/ml and the concentration of tumour necrosis factor α is about 25 ng/ml.

The T cells may be activated in vitro, for example, in a method for obtaining increased lymphokine production from a T cell culture, comprising activating the T cells according to the invention.

The T cells wherein T cells may be activated in vivo, leading to an enhanced immunological response which may be used in a method of therapy comprising activating in a human or animal subject T cells using the method according to the invention.

In this aspect of the invention, the combination of cytokines acts as an adjuvant enhancing the T-cell response and thereby enhancing the immune response.

T cells can be activated to produce desirable lymphokines useful in cell-mediated immune responses, such as interleukins, interferons and colony stimulating factors, without the problems associated with antigen dependent activation.

Additionally, it will be possible to achieve isolated T cell activation and effector T cell recruitment in areas of specific immunological interest without the use of antigens. This will thus be extremely useful for the in vivo treatment of numerous diseases and infections such as HIV and Hepatitis.

The present invention has the advantages of activating "by-stander" T cells, not just specifically one particular stimulating antigen, thus a bigger immune response is produced leading to the production of more lymphokines and subsequently greater immunoglobulin production by B cells.

Another advantage of the present invention is the maintenance of the peripheral pool of memory T cells as memory T cells can be expanded (proliferated) without the need of specific antigenic stimulation to maintain the clonal size. Also the naive T cell repertoire can be maintained, as the present invention allows the proliferation of naive T cells without them switching to the memory phenotype, unlike in antigenic stimulation.

According to a further aspect of the invention there is provided a pharmaceutical composition comprising two or more of the following:
 i) interleukin-2;
 ii) interleukin-6; and
 iii) tumour necrosis factor α
or functionally equivalent fragments thereof optionally in association with one or more pharmaceutically acceptable excipients.

The pharmaceutical composition may itself be useful for the therapeutic activation of T-cells or may be administered with a further therapeutic agent such as a vaccine. Administration may be simultaneous or sequential.

According to the present invention there is provided a method of gene therapy comprising the step of administering a vector carrying a genes encoding two or more of i) interleukin-2;
ii) interleukin-6; and
iii) tumour necrosis factor α or functionally equivalent fragments thereof.

Suitable such vectors are well known in the art[1].

According to a further aspect of the invention, there is provided a combined method of therapy comprising coadministration of a vector carrying a gene encoding one or more of i) interleukin-2;
ii) interleukin-6; and
iii) tumour necrosis factor α or functionally equivalent fragments thereof
and one or more of i) interleukin-2;
ii) interleukin-6; and
iii) tumour necrosis factor α proteins or functionally equivalent fragments thereof.

Such maintenance of specific T cell types is extremely advantageous when working with T cell cultures.

Many other uses and advantages can be seen for the present invention and such uses and advantages would be apparent to one skilled in the art.

DETAILED DESCRIPTION OF EMBODIMENT

Materials and Methods

Purification of Resting T Cells

Figure 1A:
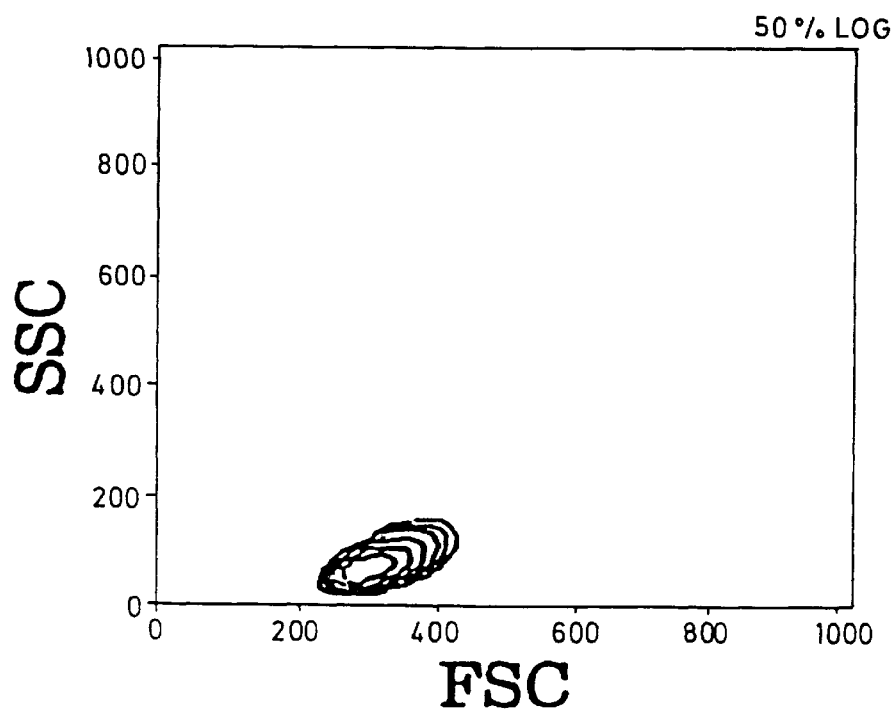
FIG. 1. Phenotypic and cell cycle analysis of purified CD4+ resting T cells. (A) forward and side scatter profile. (B) Cell cycle analysis. (C) FITC- or PE-conjugated control antibodies. (D–F) Purity of CD4+ cells and expression of activation markers. (G) Expression of CD45RA and CD45RO Ags on sorted CD4+ cells. (H and I) CD4+ cells purified as CD45RO+ or CD45RA+ subpopulations.
Figure 1B:
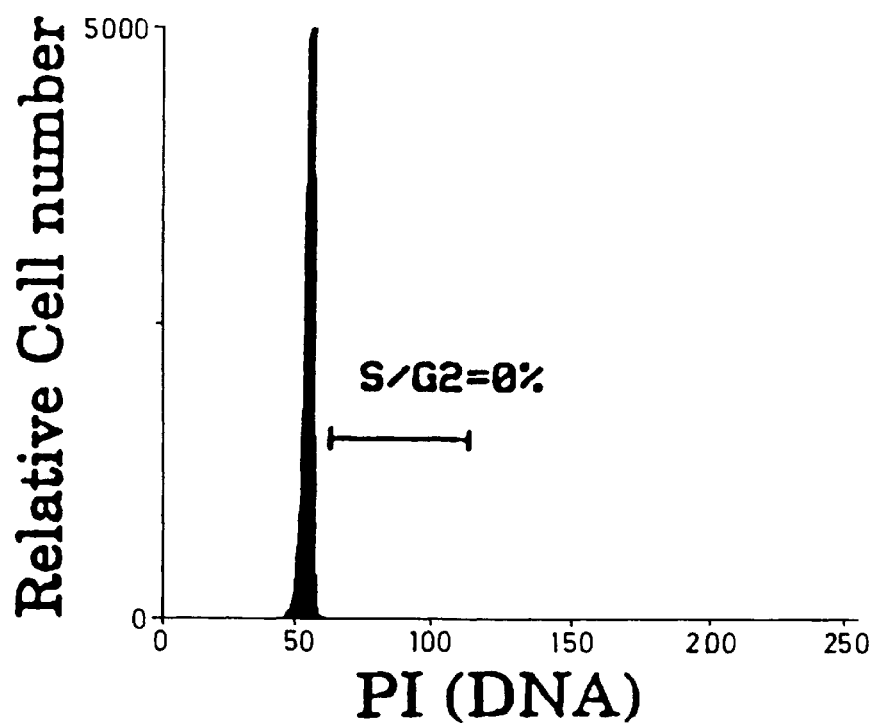
Figure 1C:
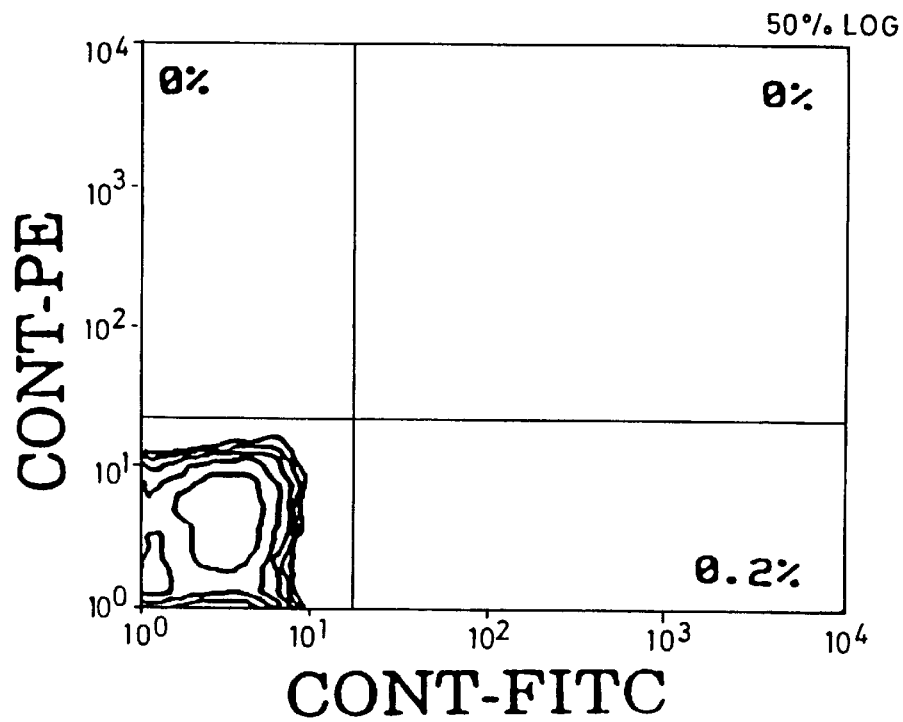
Figure 1D:
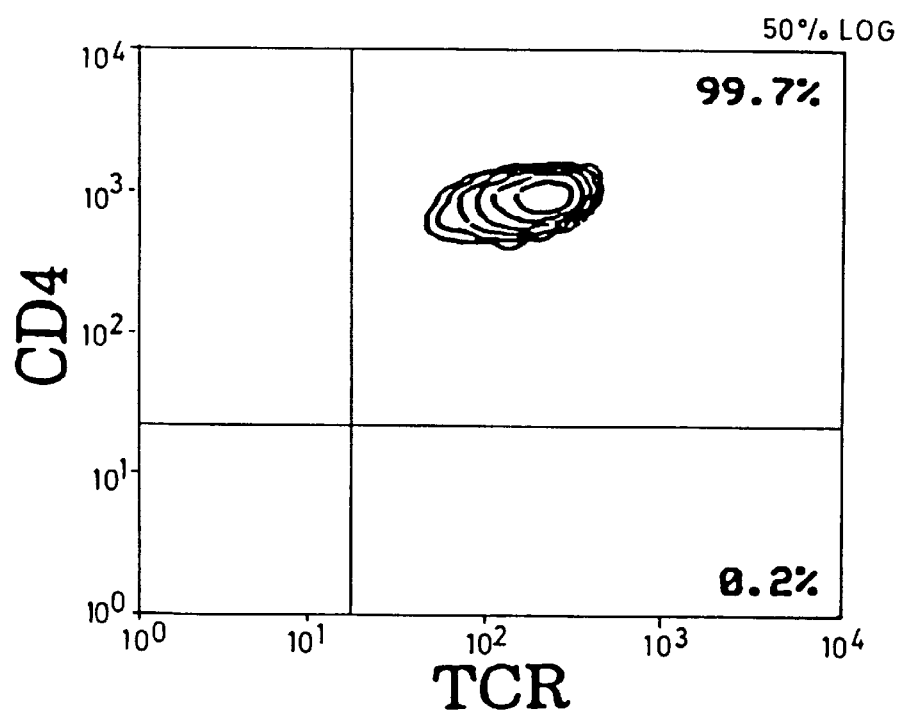
Figure 1E:
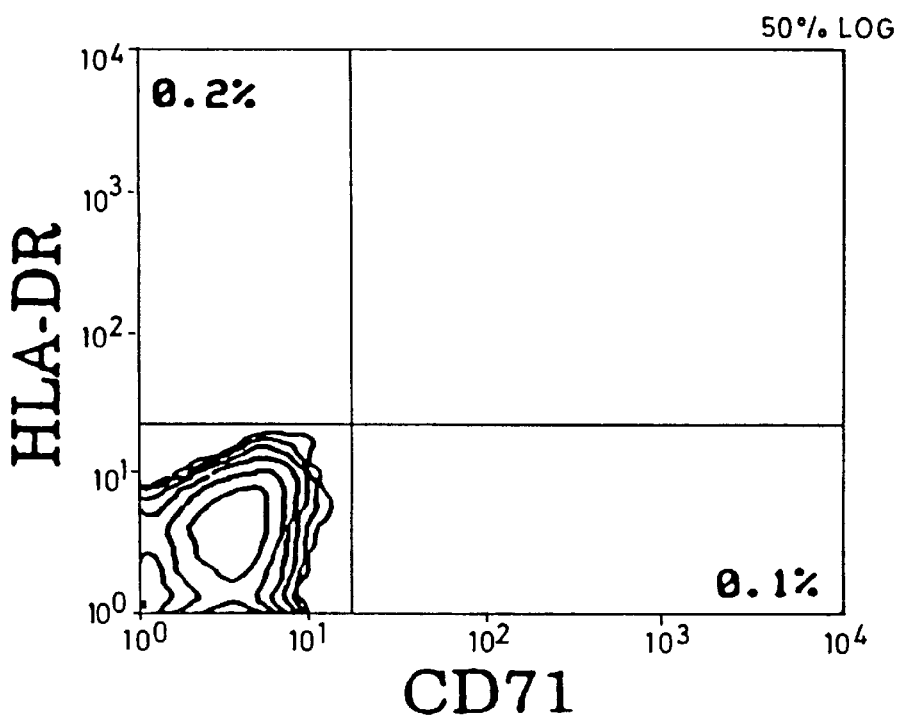
Figure 1F:
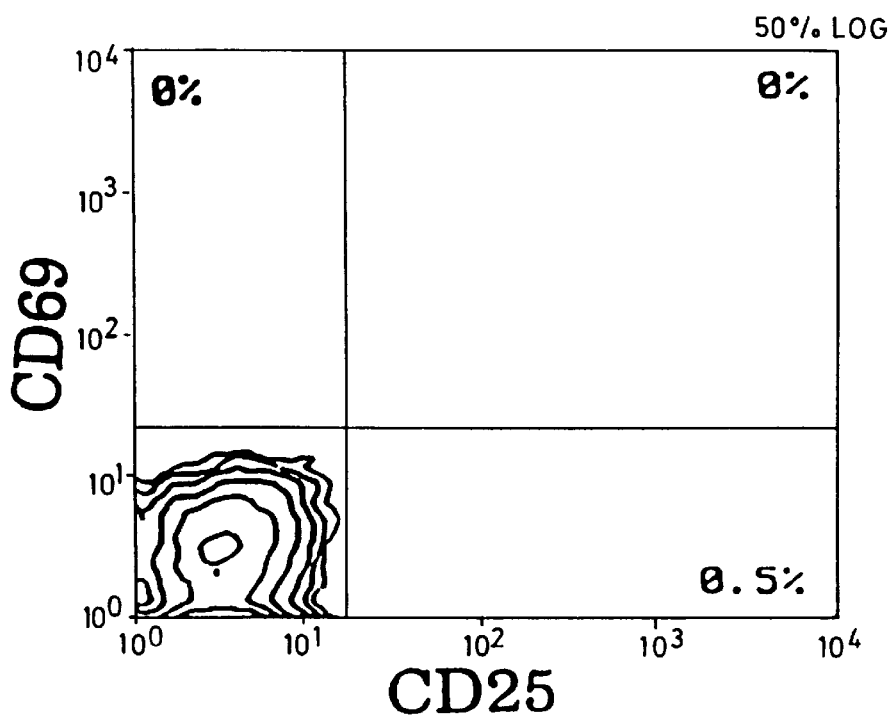
Figure 1G:
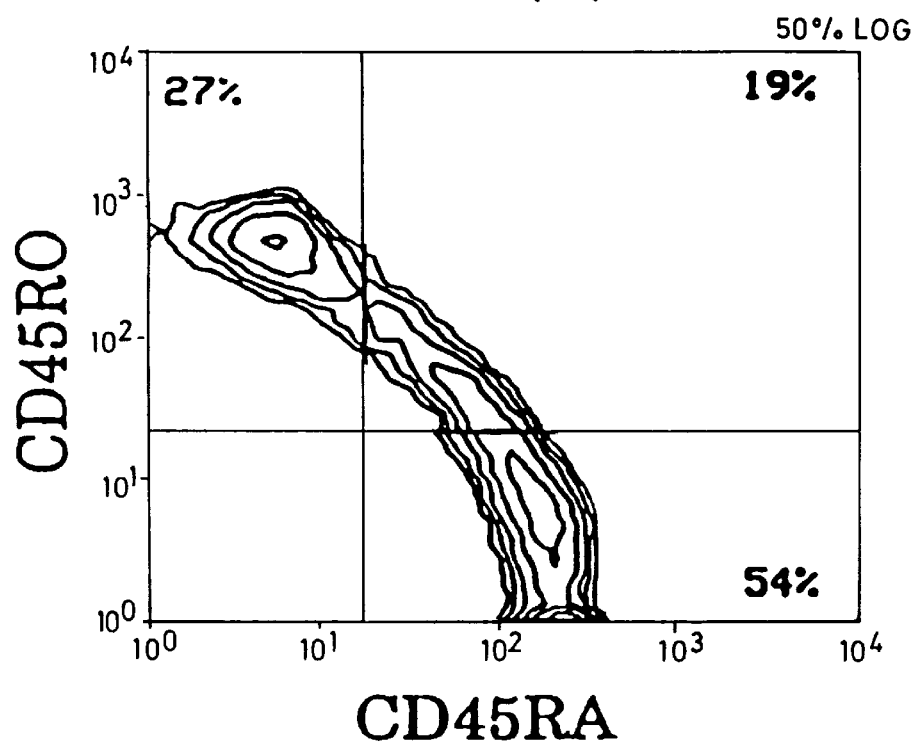
Figure 1H:
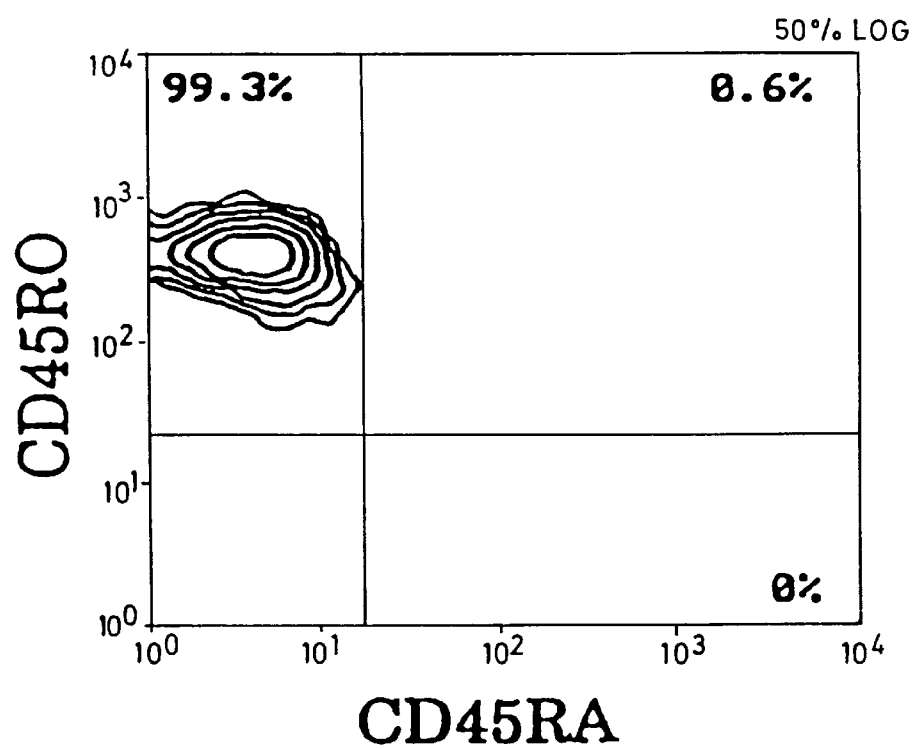
Figure 1I:
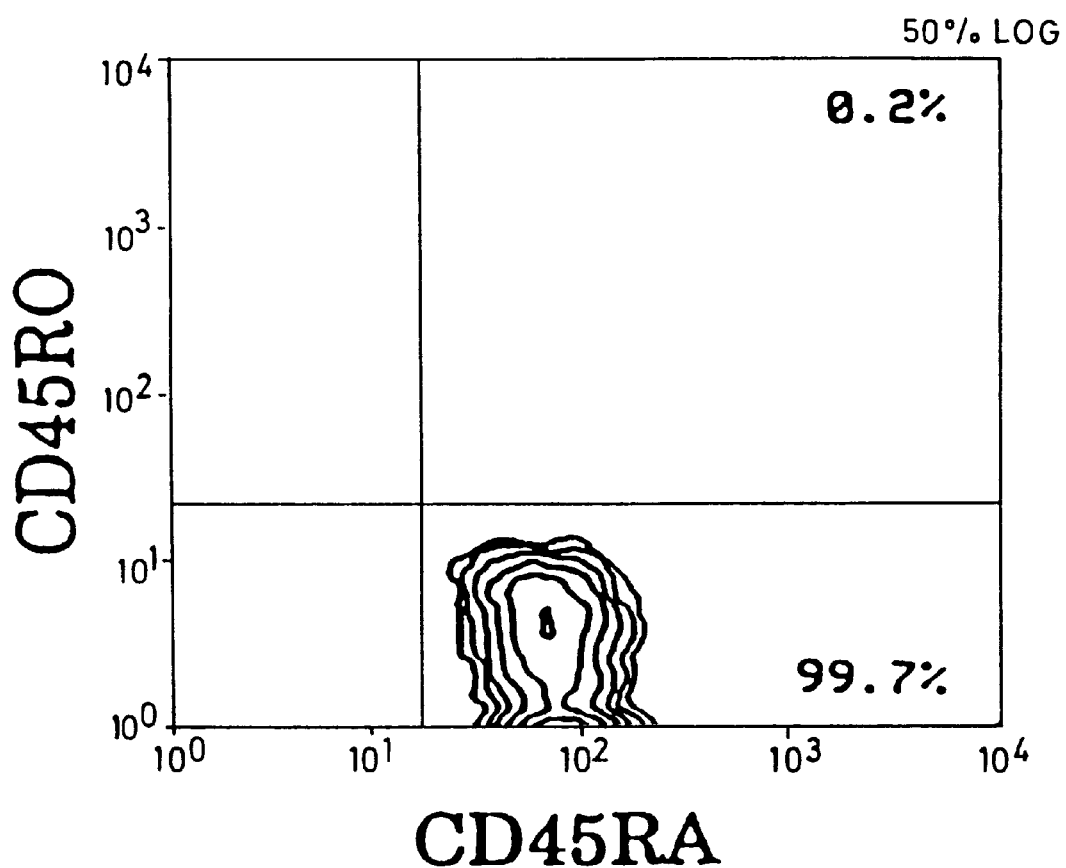

After Ficoll-Hypaque (Pharmacia) separation of PBMC from buffy coats of healthy donors, most macrophages were removed by plastic adherence. To obtain a pure resting CD4+ T cell population, cells were incubated with a cocktail of mAbs against HLA-DR (L-243; American Type Culture Collection [ATCC], Rockville, Md.), CD19 (4GT), CD16 (B73.1), CD56 (MY31), CD57 (HNK-1, ATCC), CD8 (OKT8, ATCC), CD11b (OKM-1, ATCC), CD14 (MØ-P9), TCR-c/δ (B1, a gift of G. De Libero, ZLF Basel, Switzerland), CD25 (2A3), CD69 (L78), and CD71 (L01.1). After 30-min incubation on ice, cells were washed twice and incubated with magnetic beads (Dynabeads; Dynal, Oslo, Norway) conjugated with goat anti-mouse IgG and rat anti-mouse IgM, at a 1:4 target/bead ratio. After 30-min incubation, bead-bound cells were removed using rare earth magnet (Advanced Magnetics, Inc., Cambridge, Mass.). Remaining cells were further purified with four more incubations with beads at increasing target/bead ratios (1:10 to 1:100). Final population was used as a source of resting CD4+ T cells when >99.3% of the population was TCRα/β+ (WT/31) and CD4+ (Leu 3a), as determined by immunofluorescence analyses using a FACScan® flow cytometer (Becton Dickinson & Co., Mountain View, Calif.), and fulfilled the following criteria; (a) small size at the FACS® scatter; (b) absence of FACS®-detectable levels of the activation markers (CD69, CD71, MHC-DR and IL-2 receptor p55 chain (CD25); (c) absence of cells in the S and G$_2$/M parts of the cell cycle; and (d) no significant incorporation of [$^3$H]thymidine when exposed to IL-2. In some experiments resting cells were further negatively sorted as CD45RO− (adding the mAB UCHl-1) or CD45RA− (adding the mAB L48). If not otherwise indicated, all the mAbs were from Becton Dickinson & Co.

Preparation of Supernatants

T cells (5×10$^3$/ml) from a tetanus toxoid (TT)-specific clone were cultured with autologous macrophages (2.5×10$^5$/ml) that had been prepulsed with or without TT (3 μg/ml) (Biocine Sclavo, Siena, Italy). After 16 h, supernatants were collected and filtered with 0.2-μm filters. Culture medium has been previously described (3) using 5% human serum or plasma. Effective supernatants were prepared using medium with either 5% human serum (from Florence blood bank) or serum-free media (HL-1: Ventrex, Portland, Oreg.). Similar results were obtained with resting T cells derived from PBMC of six different healthy individuals and with supernatants from activated CD4+ T cell clones, with different specificity (purified protein derivatives [PPD] or pertussis toxin), from four different persons (see FIG. 2 and data not shown).

Cell Cycle Analysis

This was performed as described (4) using propidium iodide in combination with anti-CD4 mAb (FITC labelled) staining. Analyses were performed with the FACScan® Lysis II software and doublet discrimination program (Becton Dickinson & Co.).

Purification of B Cells

PBMC-derived B cells were stained with FITC-labelled anti-CD19 mAb and purified by positive sorting with FACStar® (Becton Dickinson & Co). Purity was >98% as determined by staining with anti-CD20 and anti-Ig.

Helper Assay

Noncognate helper assays were performed as previously described (5). Briefly, purified autologous PBMC-derived B cells ($2 \times 10^3$/well) were cocultured for 12 d with $CD4^+$ $CD45RO^+$ resting T cells ($3 \times 10^4$/well) in the presence of cytokine combinations as described (see FIG. 3) or on anti-CD3-coated plates. To avoid an effect of cytokines on B cell differentiation, plates were washed after 4-d culture and cytokine combinations were replaced with IL-2 alone. Ig in the supernatants was measured by ELISA (5).

Activation of Resting T cells by Supernatants

Resting T cells were cultured in 96-well flat-bottom plates ($5 \times 10^4$/well) with supernatant (50% vol/vol) from T cell clones cultured with autologous macrophages prepulsed with Ag, medium or rIL-2 (Cetus Corp., Emeryville, Calif.) at a concentration corresponding to that found in the T cell supernatants (i.e. 200–300 U/ml). Activation was measured at various time points as expression of CD69 and CD25 of [$^3$H]thymidine incorporation. In some experiments, [$^3$H] thymidine incoporation of resting $CD45RO^+$ or $CD45RA^+$ T cells was measured in the presence of different concentrations of IL-2 plus either 1 $\mu$g/ml LPS (Difco, Detroit, Mich.) or supernatant (50% vol/vol) from LPS-activated macrophages. For the preparation of activated macrophage supernatant, $5 \times 10^5$ macrophages were simulated with 1 $\mu$g/ml LPS (for 6–8 h). [$^3$H]Thymidine incorporation experiments were performed as described (5). The results represent the mean of triplicate wells and SD was always 15%.

Activation of Resting T Cells by Recombinant Cytokines

Resting T cells ($5 \times 10^4$/well) in 96-well flat-bottom microplates were cultured for 8 d with various combinations of the following rIL-2 (200–300 U/ml), rIL-6 (500 U/ml; Ciba-Geigy, Basel, Switzerland; IL-6 units were determined with the B9 assay), TNF-$\alpha$ (25 ng/ml; Genzyme Corp., Cambridge, Mass.), and supernatant (50% vol/vol) from LPS-stimulated macrophages. Thymidine incorporation and CD69 expression were measured as described in FIG. 2. IL-1b (up to 100 ng/ml, Biocine Sclavo Siena, Italy) in combination with IL-2 and TNF-$\alpha$ did not have any activities (data not shown). Recombinant cytokines from two different sources have been used with similar results. The optimal concentration of cytokines was established in preliminary dose-response experiments.

PCR-assisted mRNA Amplification

Purified resting $CD4^+$ $CD45RO^+$ T cells were cultured with TNF-$\alpha$ plus IL-6 plus IL-2, or IL-2 alone. Total RNA was isolated after 60–100 h of culture from $5 \times 10^5$ cells, by RNAzol* B (Biotecx Laboratories, Houston, Tex.). cDNA was synthesized with murine reverse transcriptase as described (5). $\beta$-actin, IL-4, and IFN-c specific primer pairs were purchased from Clontech (Palo Alto, Calif.). PCR was performed as described (5).

Limiting Dilution Analyses $CD45RO^+$ resting T cells were plated at different numbers in Terasaki plates (64 wells per condition) in 20$\mu$l vol in the presence of purified autologous irradiated (2,500 rad) macrophages ($3 \times 10^3$/well)m anti-DR mAb (L243, 20 $\mu$g/ml) with IL-2 alone (300 U/ml) or in combinations with TNF-$\alpha$ (25 ng/ml) and IL-6 (500 U/ml). On day 14, cultures were visually inspected for growth. Randomly selected growing wells were positively stained with anti-CD4 and anti-TCR-$\alpha/\beta$ antibodies. Frequency analyses were done by the least squared method (6).

Results and Discussion

Figure 2:
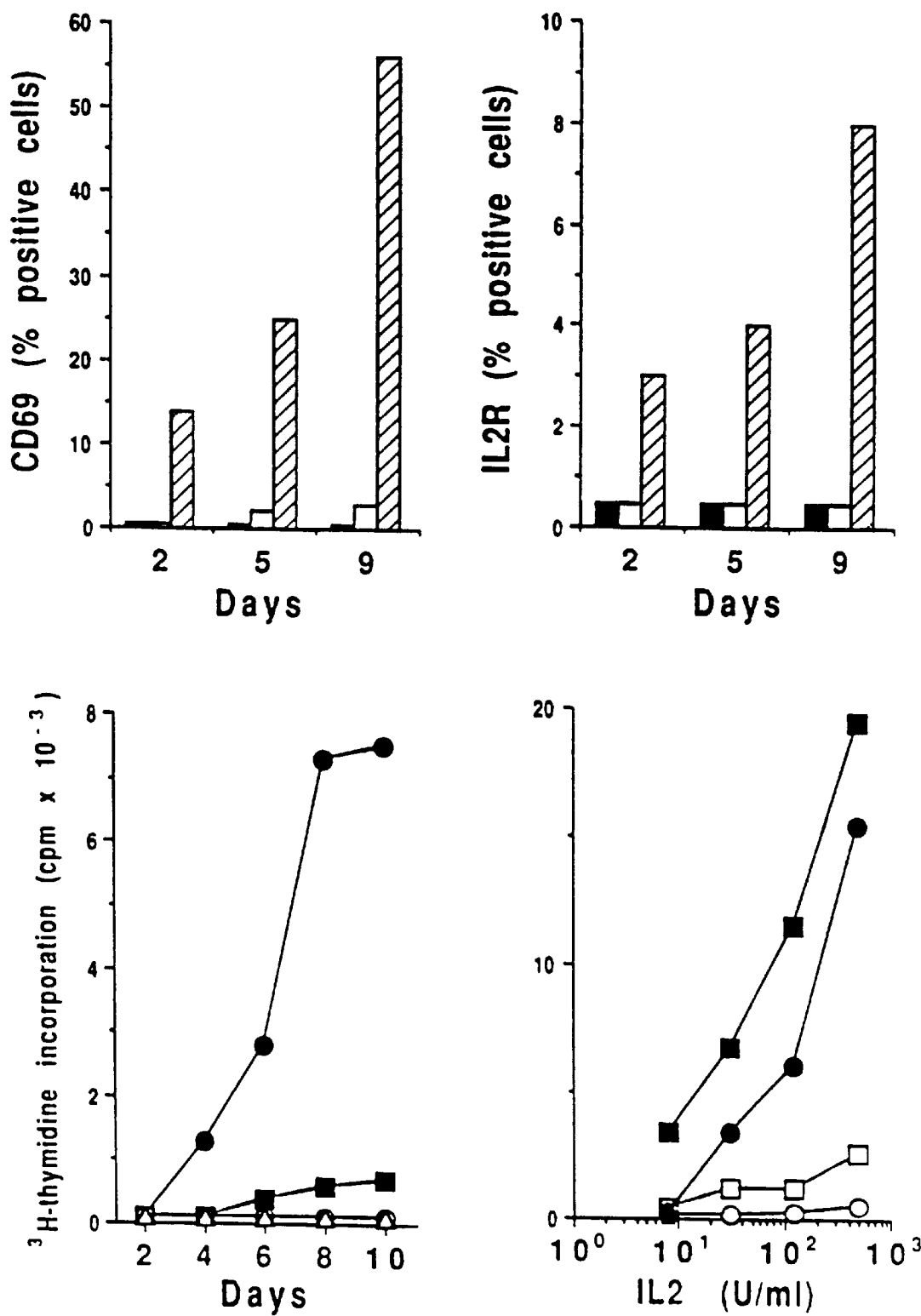
FIG. 2. Activation of resting CD4+ T cells by soluble factors. (A and B) Expression of activation markers on resting T cells cultured with supernatant from T cell clones cultured with autologous macrophages prepulsed with Ag (hatched bars) or medium (solid bars), or rIL-2 (open bars). Expression of CD69 or CD25 was analyzed in double staining with anti-CD4. (C) [$^3$H]Thymidine incorporation of the same cells in A and B, cultured with medium alone (triangles), rIL-2 (squares), or supernatant from a T cell clone cultured with macrophages prepulsed with Ag (closed circle) or medium (open circle). (D) [$^3$H]Thymidine incorporation of resting CD45RO+ (squares) or CD45RA+ (circles) T cells in the presence of different concentration of IL-2 plus 1 μg/ml LPS (open symbols), or IL-2 with supernatant from LPS-activated macrophages (closed symbols).

A critical point of this study was to use a resting population devoid of activated T cells that would respond to IL-2 alone. We chose to work with resting $CD4^+$ T cells because, at variant with some $CD8^+$ or c/$\delta$ T cells with resting phenotype, they do not express IL-2 receptor p75-chain in the absence of the p55-chain (7), which may be responsible for unwanted proliferation responses to IL-2 (8) and for which we did not have a good antibody to sort out. We therefore performed multistep exhaustive purifications to obtain highly purified resting $CD4^+$ T cells from PBMC (FIG. 1). In preliminary experiments, resting $CD4^+$ T cells were cultured with supernatants from $CD4^+$ T cell clones that had been activated with Ag-pulsed macrophages. A representative experiment in FIG. 2 shows that a fraction of resting $CD4^+$ T cells is activated by the supernatant, but not by IL-2, to express CD69 (9) (FIG. 2A) and IL-2 receptor p55-chain (FIG. 2B), and to incorporate [$^3$H]thymidine (FIG. 2C).

Since the activating supernatant is produced by the coculture of two cell types, we sought to determine the relative contribution of soluble factors produced by T cells and APCs. For this experiment, resting $CD4^+$ T cells were further purified as $CD45RO^+$ (memory) and $CD45RA^+$ (naive) subpopulation (10), since they may have different activation requirements as already reported for TCR-mediated activation (11, 12). FIG. 2D shows that supernatant from LPS-activated macrophages alone, as IL-2 alone, did not have any activity, whereas macrophage supernatant in combination with IL-2 induced thymidine incorporation in both $CD45RA^+$ and $CD45RO^+$ resting T cells. These results demonstrate that IL-2 and soluble factor(s) produced by APCs are required for the activation of resting T cells.

Figure 3A:
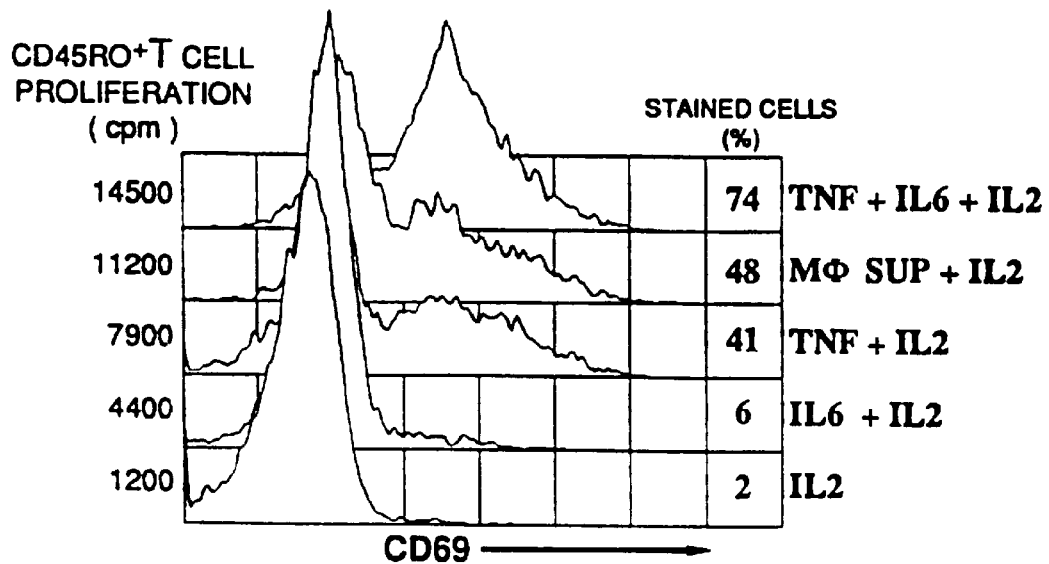
FIG. 3. Combination of IL-2, TNF-α, and IL-6 activates resting T cells. CD45RO+ (A) or CD45RA+ (B) resting T cells were cultured for 8 d with various combinations of the following: rIL-2, rIL-6, TNF-α, and supernatant from LPS-stimulated macrophages. Thymidine incorporation and CD69 expression were measured as described in FIG. 1. (C) Cell cycle analysis of resting CD45RO+ (squares) or CD45RA+ (circles) T cells in the presence of IL-2 alone (open symbols) or in combination with TNF-α and IL-6 (closed symbols).
Figure 3B:
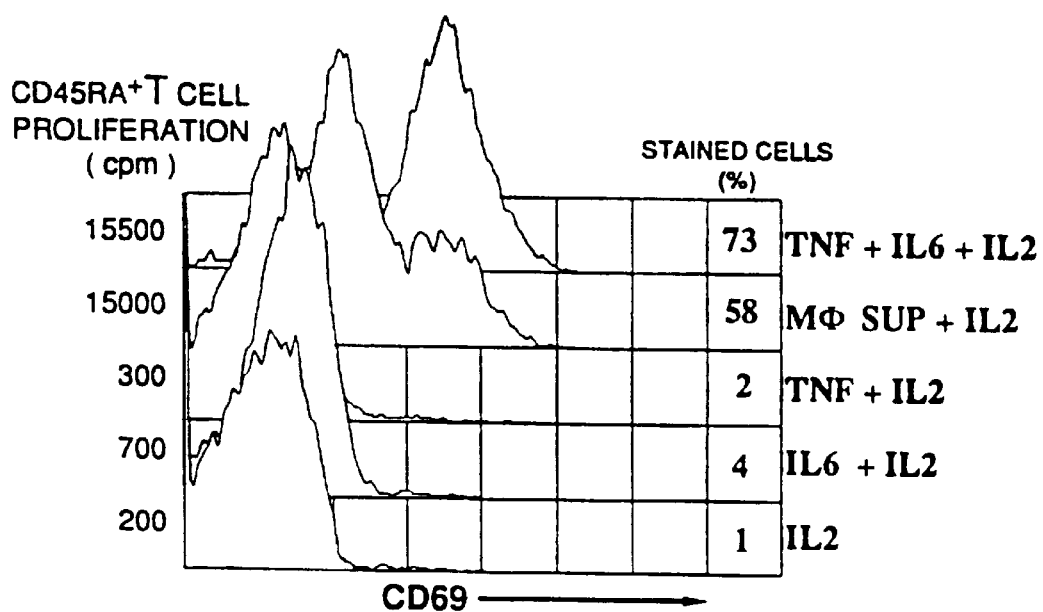
Figure 3C:
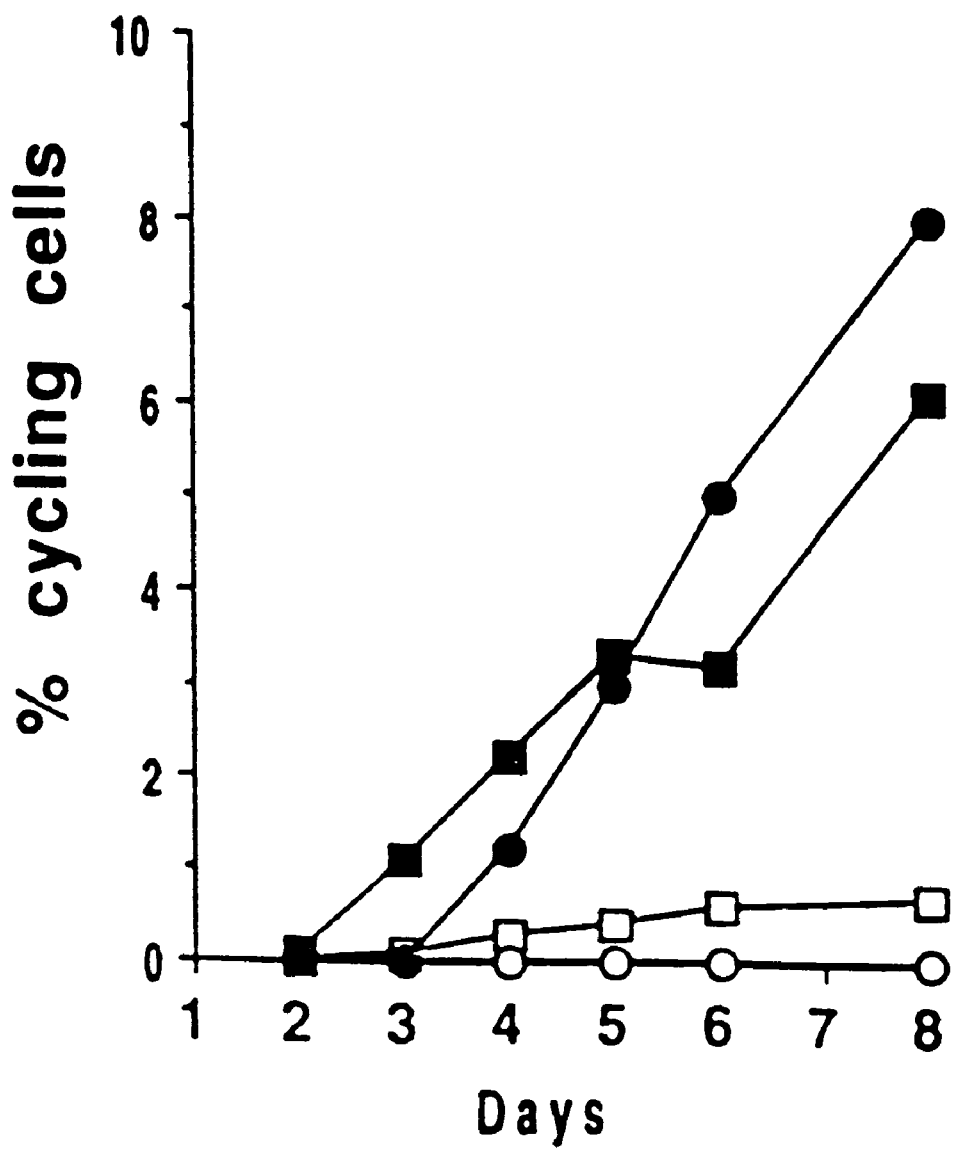

To identify the APC-derived factor(s), we tested the effect of recombinant cytokines known to be produced by macrophages and to have costimulatory activity on T cells, i.e., IL-1$\beta$, IL-6 and TNF-$\alpha$ (13–15). In the absence of IL-2 all the possible combinations of these cytokines did not show any activity over a wide range of concentrations (data not shown). FIG. 3A shows that TNF-$\alpha$ in combination with IL-2 induced resting $CD45RO^+$ T cells to express CD69 and to incorporate thymidine, whereas IL-6 in combination with IL-2 was much less effective. Remarkably, TNF-$\alpha$ and IL-6, in combination with IL-2, had a synergistic effect leading to a stronger activation. A similar effect of IL-2, IL-6, and TNF$\alpha$ was also observed on $CD45RA^+$ resting T cells (FIG. 3B), although, in this case, all three cytokines were required to induce activation. Furthermore, the cell cycle analyses in FIG. 3C show that at day 7 of culture 8% of both $CD45RO^+$ and $CD45RA^+$ T cells are in the S or $G_2$/M phases of the cell cycle. Activation of cytokines, measured as expression of activation markers, thymidine incorporation, or entry into cell cycle, was never inhibited by mAbs specific for DR, CD4, or CD3 (data not shown), thus confirming that TCR signalling is not involved in this type of activation.

Figure 4:
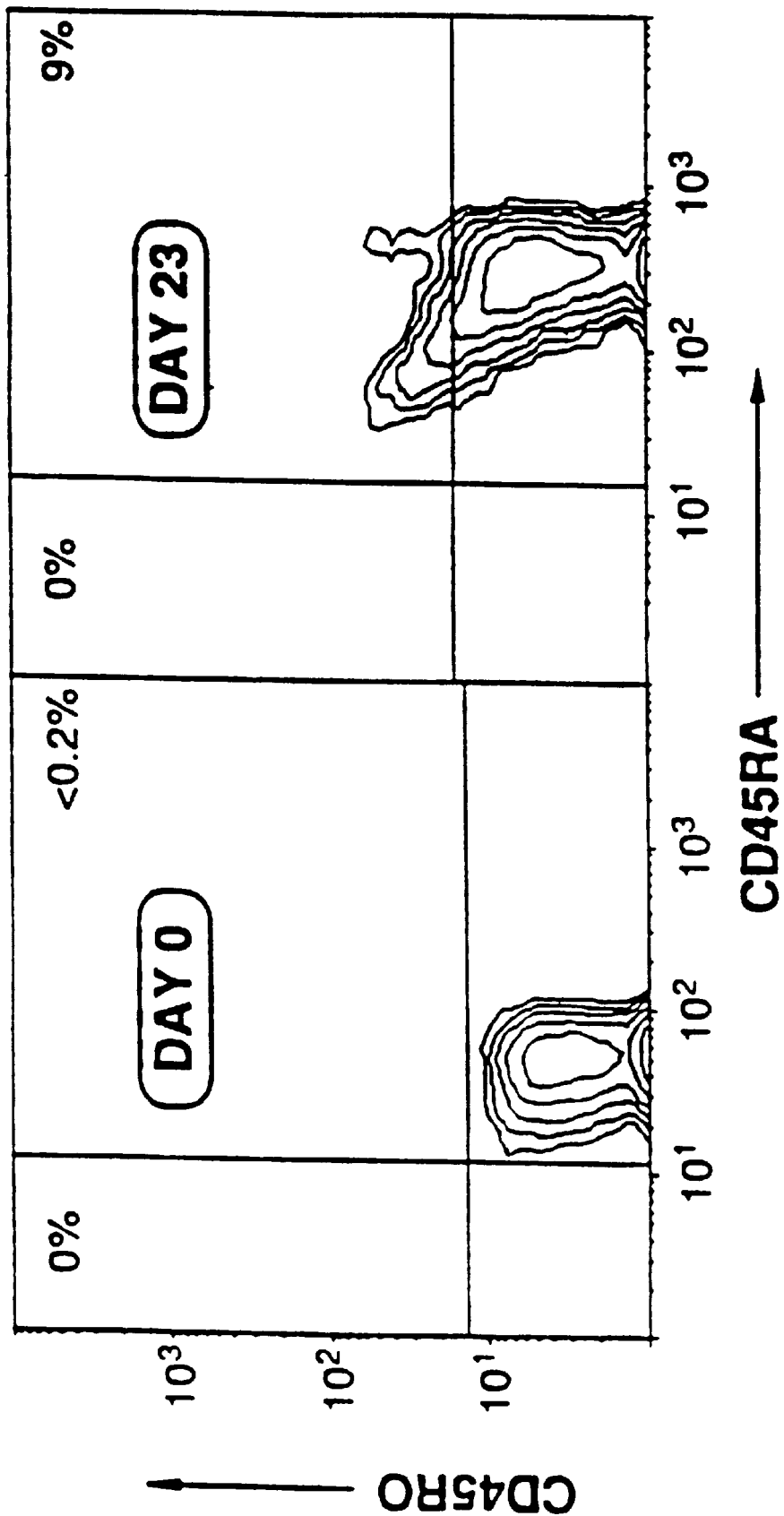
FIG. 4. CD45RA+ T cells activated by cytokines do not switch their phenotype to CD45RO. CD45RA+ T cells were activated by combination of IL-2, TNF-α, and IL-6, and after 23 days were double stained with anti-CD45RA-FITC and anti-CD45RO-PE antibodies.

It is interesting to note that we have observed that CD45RA$^+$ T cells activated by cytokines do not switch their phenotype to CD45RO, as was reported to occur within a few days after TCR engagement (16). CD45RA$^+$ T cells activated by combination of IL-2, TNF-α, and IL-6 were double stained with anti-CD45RA and anti-CD45RO antibodies at 3-d intervals up to day 23 of culture. We never found single positive CD45RO$^+$ cells at any time point, and only found a few percent of double positive CD45RA$^{+high}$/CD45RO$^{+dull}$. Indeed, FIG. 4 shows that naive T cells even 23 d after cytokine activation, when most cells are blastic and express CD69 (data not shown), are mainly CD45RA$^+$. The same cells activated with anti-CD3 switched in few days to the CD45RO$^+$ CD45RA$^-$ phenotype (data not shown).

Figure 5:
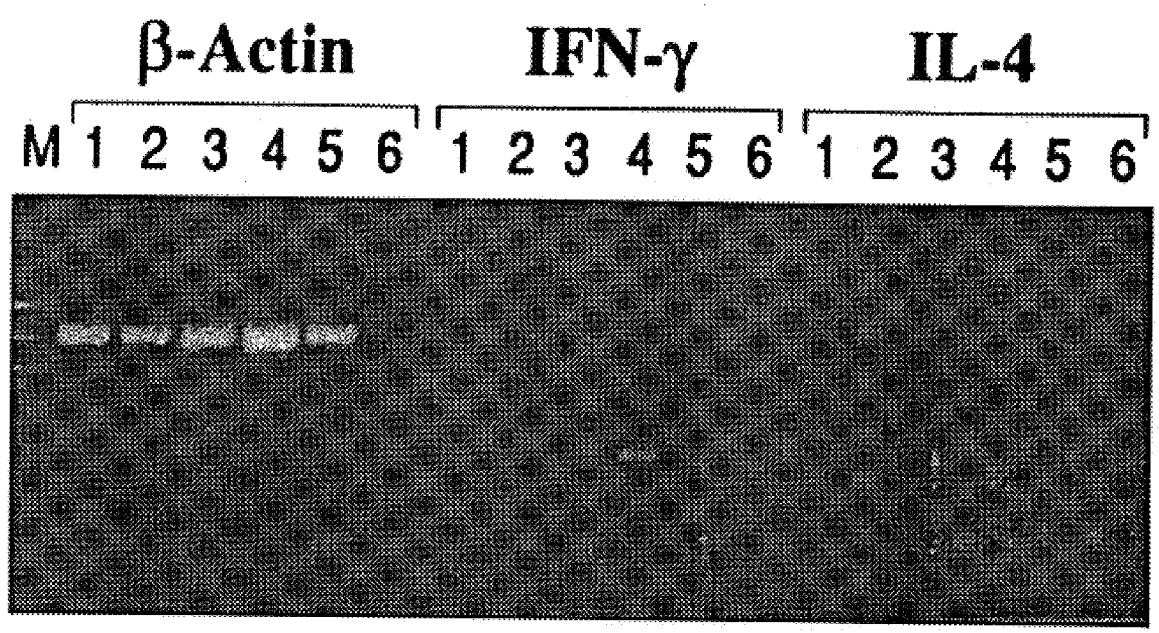
FIG. 5. Expression of IFNc and IL-4 mRNA by cytokine-activated T cells. Purified CD4+ CD45RO+ resting T cells are cultured with IL-2 alone for 60 (lane 1) and 100 h (lane 3) or with IL-2, TNF-α, and IL-6 for 60 (lane 2) and 100 h (lane 4) as described in Materials and Methods. (Lane 5) Positive template; (lane 6) negative control.

We next asked whether resting T lymphocytes can be activated by cytokines to display effector function. We performed PCR-assisted mRNA amplification for lymphokines. FIG. 5 shows that both IFN-c and IL-4 mRNA are expressed by CD45RO$^+$ T cells cultured with IL-2, TNF-α, and IL-6, but not with IL-2 alone. Moreover, CD45RO$^+$ T cells activated by cytokine combination are as effective as anti-CD3-stimulated T cells in helping B cells to produce Ig (Table 1).

|  | IgM | IgG | IA |
|---|---|---|---|
|  |  | ng/ml |  |
| B cells cocultured with: |  |  |  |
| IL-2 plus TNF-α plus IL-6 | <15 | <5 | <10 |
| T cells plus medium | <15 | <5 | <10 |
| T cells plus IL-2 | <15 | <5 | <10 |
| T cells plus IL-2 plus TNF-α | 32 | 23 | <10 |
| T cells plus IL-2 plus IL-6 | <15 | 31 | 28 |
| T cells plus IL-2 plus TNFα plus IL-6 | 75 | 274 | 308 |
| T cells plus anti-CD3 mAb plus IL-2 | 235 | 219 | 413 |

To exclude the possibility that T cell help to B cells could be due to activation of autoreactive cells, at the end of the helper assay, the B cells were removed by sorting, and the CD4$^+$ T cells were tested in proliferation against autologous purified B cells or macrophages. We never found any autoreactive proliferation (data not shown).

Neither cytokines nor anti-CD3 induced CD45RA$^+$ T cells to produce IFN-c (<1 IU/ml) and to help B cells (data not shown). Thus, we conclude that, similar to TCR-mediated activation (17), cytokines recruit CD45RA$^+$ T cells to proliferate but not to help Ig production, whereas they activate resting CD45RO$^+$ T cells to proliferate and display effector functions.

Figure 6:
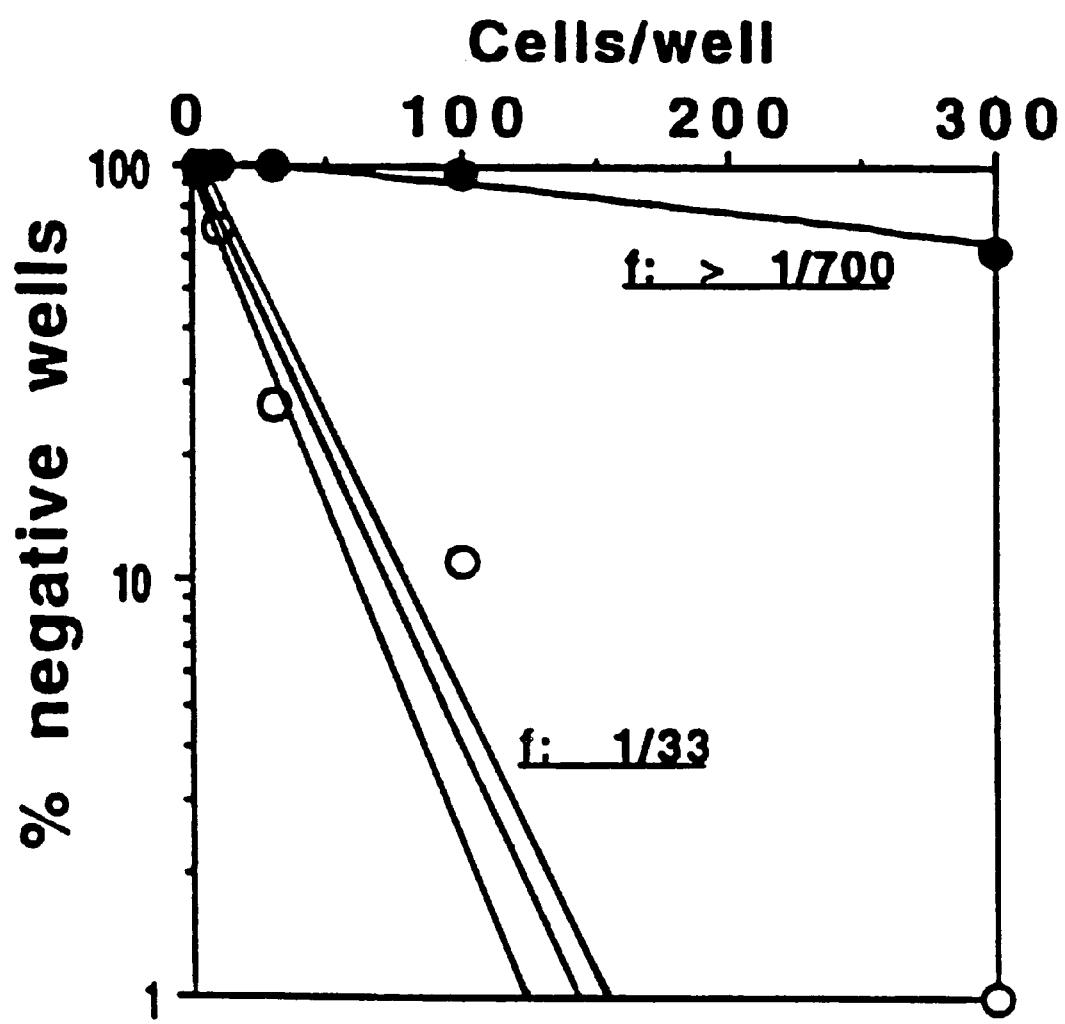
FIG. 6. Frequency of resting T cells that grow in response to cytokine combination. CD45RO+ resting T cells were plated in the presence of purified autologous macrophages, anti-DR mAb with IL-2 alone (closed circles) or in combination (open circles) with TNF-α and IL-6. (Dotted lines) 95% confidence limits.

To evaluate the frequency of resting T cells with memory phenotype that could be stimulated by cytokines to grow, we performed limiting dilution experiments. CD45RO$^+$ CD4$^+$ resting T cells were cultured with IL-2 alone or in combination with TNF-α and IL-6, in the presence of autologous irradiated macrophages and anti-DR antibodies to prevent autoreactive responses. FIG. 6 shows that 1 of 33 resting CD45RO$^+$ CD4$^+$ T cells grew to a visible clone in response to IL-2, TNF-α. and IL-6. At present we do not know why only 3% of cells grew in response to cytokines. The cells that proliferated could have been a subset of resting T cells or could have been at a different stage of maturation/activation. It is possible that many cells (≈20%) respond to cytokines and express activation markers. Some of these cells will display effector functions and only a minority (3%) will be able to grow in vitro to a clone of visible size.

TNF-α and IL-6 both have been shown to upregulate IL-2R expression on T cells (15, 18). This could be a possible mechanism for the activation of resting T cells by this cytokine combination. However, resting T cells cultured for 1–3 d with TNF-α and IL-6, and washed and cultured for 4–5 d more with IL-2, did not show FACS®-detectable levels of IL-2R (p55) (data not shown), whereas IL-2R was expressed on ≈20% of the same cells cultured with TNF-α, IL-6, and IL-2 from the beginning of the culture. This experiment, however, does not rule out the possibility that low levels of IL-2R below the FACS® sensitivity, are expressed and functionally relevant. Indeed, it has been reported that Il-2 is required for induction of IL-2R by TNF-α or IL-6 (19). Furthermore, IL-2 augments not only expression of its own receptor (20) but also upregulates TNF-α receptor (21). Elucidation of the mechanism of activation of resting T cells by cytokines will require additional biochemical and molecular analyses.

This novel Ag-independent pathway of T cell activation may play two important roles in vivo, by recruiting effector T cells at the site of immune response and by maintaining the peripheral pool of memory T cells. A scenario could be depicted where resting T cells at sites of Ag-specific response are activated by cytokines produced by specific T cells and macrophages to proliferate and to secrete other lymphokines that can further amplify the response. Indeed, the frequency of resting CD45RO$^+$ T cells that respond to cytokine combination is definitely higher than the usual frequency of T cells primed by any known Ags.

It has been postulated that memory can be carried by long-lived clones consisting of short-lived cells that require repeated, intermittent stimulation by persisting Ag, by recurrent infection, or by cross-reacting environmental Ags (22–24). In the light of our results, it is tempting to speculate that memory T cells may not require antigenic stimuli to maintain their clonal size, since resting T cells with memory phenotype (CD45RO$^+$) can be expanded by cytokines secreted during responses to unrelated antigens. On the other hand, cytokines can induce proliferation of naive cells without switch to memory phenotype and may therefore help to maintain the naive (CD45RA$^+$) T cell repertoire.

It will be understood that the invention is described above by way of example only and modifications within the scope and spirit of the invention may be made.

REFERENCES

1. Carding, S. R. W. Allan, A. McMile, and P. Doherty, 1993. Activation of cytokine genes in T cells during primary and secondary murine influenza. *J. Exp. Med.* 177:475.
2. Grossman, Z., and W. E. Paul. 1992. Adaptive cellular interactions in the immune system: the tunable activation threshold and the significance of subthreshold responses. *Proc. Natl. Acad. Sci. USA.* 89:10365.
3. Abrignani, S., D. Montagna, M. Jeannet, J. Wintsch, N. L. Haigwood, J. R. Shuster, K. S. Steimer, A. Cruchaud, and T. Staehelin. 1990. Priming of CD4$^+$ T cells specific for conserved regions of human immunodeficiency virus glycoprotein gp120 in humans immunized with a recombinant envelope protein. *Proc. Natl. Acad. Sci. USA.* 87:6136.
4. Schmid, I., C. H. Uittenbogaart, and J. V. Giorgi. 1991. A gentle fixation and permeabilization method for combined cell surface and intracellular staining with improved precision in DNA quantification. *Cytometry.* 12:279.

5. Minutello, M., P. Pileri, D. Unutmaz, S. Censini, G. Kuo, M. Houghton, M. R. Brunetto, F. Bonino, and S. Abrignani. 1993. Compartmentalization of T lymphocytes to the site of disease:intraheptic CD4+ T cells specific for the protein NS4 of hepatitis C virus in patients with chronic hepatitis C. *J. Exp. Med.* 178:17.
6. Lefkovits, I., and H. Waldmann. 1984. Limiting dilution analysis of the cells of the immune system. I. The clonal basis of the immune response. *Immunol. Today.* 5:262.
7. Tsudo, H., F. Kitamura, and M. Miyasaka. 1989. Characterization of the interleukin 2 receptor β chain using three distinct monoclonal antibodies. *Proc. Natl. Acad. Sci. USA.* 86:1982.
8. Smith, K. A. 1993. Lowest dose interleukin-2 immunotherapy. *Blood.* 81–1414.
9. Testi, R., J. H. Phillips and L. L. Lanier. 1989. Ley23 induction as an early marker of function CD3/T cell antigen receptor triggering: requirement for receptor crosslinking, prolonged elevation of intracellular $Ca^{2+}$ and activation of PKC. *J. Immunol.* 142:1854.
10. Akbar, A. N., L. Terry, A. Timms, P. Beverley, and G. Janossy. 1988. Loss of CD45R and gain of UCHL1 reactivity is a feature of primed T cells. *J. Immunol.* 140:2171.
11. Byrne, J. A., J. Butler, and M. D. Cooper. 1988. Differential activation requirements for virgin and memory T cells. *J. Immunol.* 141:3249.
12. Horgan, K. J., G. A. Seventer, Y. Shimizu, and S. Shaw. 1990. Hyporesponsiveness of "naive" (CD45RA+) human T cells to multiple receptor-mediated stimuli but augmentation of responses by co-stimuli. *Eur. J. Immunol.* 20:1111.
13. Weaver, C. T., and E. R. Unanue. 1990. The costimulatory function of antigen presenting cells. *Immunol. Today.* 11:49.
14. Garman, R. D., K. A. Jacobs, S. T. Clark, and D. H. Raulet. 1987. B cell-stimulatory 2 ($β_2$ interferon) functions as a second signal for interleukin 2 production by mature murine T cells. *Proc. Natl. Acad. Sci. USA.* 84–7629.
15. Scheurich, P., B. Thoma, U. Ucer, and K. Pfizenmaier. 1987. Immunoregulatory activity of recombinant human tumor necrosis factor TNFα: Induction of TNF receptors on human T cells and TNF-α-mediated enhancement of T cells responses. *J. Immunol.* 138:1786.
16. Akbar, A. N., A. Timms, and G. Janossy. 1989. Cellular events during memory T cell activation in vitro: the UCHL1 determinant is newly synthesized after mitosis. *Immunology.* 66:213.
17. Sleasman, J. W., C. Morimoto, S. F. Schlosman, and T. F. Tedder. 1990. The role of functionally distinct helper T lymphocyte subpopulations in the induction of human B-cell differentiation. *Eur. J. Immunol.* 20:1357.
18. Shizuo, A., T. Hirano, T. Taga, and T. Kishimoto. 1990. Biology of multifunctional cytokines: IL-6 and related molecules (IL-1 and TNF). FASEB (*Fed. Am Soc. Exp. Biol*) *J.* 4:2860.
19. Vink, A., C. Uyttenhove, P. Wauters and J. V. Snick. 1990. Accessory factors involved in murine T cell activation. Distinct roles of interleukin 6, interleukin 1 and tumor necrosis factor. *Eur. J. Immunol.* 20:1.
20. Depper, J. M., W. J. Leonard, C. Drogula, M. Kronke, T. A. Waldmann, and W. C. Green. 1985. Interleukin 2 (IL-2) augments transcription of the IL-2 receptor gene. *Proc. Natl. Acad. Sci. USA.* 82:4230.
21. Owen-Schaub, L. B., W. L. Crump III, G. I. Morin, and E. A. Grimm. 1989. Regulation of lymphocyte tumor necrosis factor receptors by IL-2. *J. Immunol.* 143:2236.
22. Beverley, P. 1990. Is T cell memory maintained by crossreactive stimulation? *Immunol. Today.* 11:203.
23. Gray, D. 1993. Immunological memory: a function of antigen persistence. *Trends in Microbiology.* 1:39.
24. Bradley, L. M., M. Croft, and S. L. Swain. 1993. T cell memory: new perspectives. *Immunol. Today.* 14:197.

I claim:

1. A method for antigen independent activation of T cells in vitro comprising contacting T cells in the absence of antigen with a combination of at least two cytokines selected from the group consisting of interleukin-2, interleukin-6, and tumor necrosis factor alpha, or functionally equivalent fragments thereof.

2. The method of claim 1, wherein the T cells are naive T cells and/or memory resting T cells.

3. The method of claim 1, wherein the T cells are naive CD45RA+ cells and/or memory resting CD45RO+ cells.

4. The method of claim 1, wherein the concentration of interleukin-2 is from 100 to 400 U/ml, the concentration of interleukin-6 is from 400 to 600 U/ml and the concentration of tumour necrosis factor α is from 15 to 35 ng/ml.

5. The method of claim 1, wherein the concentration of interleukin-2 is from 200 to 300 U/ml, the concentration of interleukin-6 is about 500 U/ml and the concentration of tumour necrosis factor α is about 25 ng/ml.

6. The method of claim 1 wherein said T cells are contacted with interleukin-2 and tumor necrosis factor.

* * * * *

UNITED STATES PATENT AND TRADEMARK OFFICE
CERTIFICATE OF CORRECTION

PATENT NO. : 6,074,635
DATED : June 13, 2000
INVENTOR(S) : Sergio Abrignani

It is certified that error appears in the above-identified patent and that said Letters Patent are hereby corrected as shown below:

In the Assignee: Please delete "Chiron Corporation, Emeryville, Calif."
and insert --Chiron S.p.A., Siena ITALY--.

Signed and Sealed this

Eighth Day of May, 2001

NICHOLAS P. GODICI

*Attest:*

*Attesting Officer*    *Acting Director of the United States Patent and Trademark Office*